United States Patent [19]

Jørgensen

[11] Patent Number: 5,733,753

[45] Date of Patent: Mar. 31, 1998

[54] AMPLIFICATION OF GENOMIC DNA BY SITE SPECIFIC INTEGRATION OF A SELECTABLE MARKER CONSTRUCT

[75] Inventor: Steen Troels Jørgensen, Allerød, Denmark

[73] Assignee: Novo Nordisk A/S, Bagsvaerd, Denmark

[21] Appl. No.: 751,282

[22] Filed: Nov. 18, 1996

Related U.S. Application Data

[63] Continuation of Ser. No. 432,164, May 12, 1995, abandoned.

[30] Foreign Application Priority Data

Dec. 22, 1992 [DK] Denmark ............... 1539/92

[51] Int. Cl.$^6$ ............... C12P 19/34; C12Q 1/68; C07H 21/02

[52] U.S. Cl. ............... 435/91.4; 435/6; 435/91.2; 435/172.3; 435/91.1; 536/22.1; 536/23.1; 536/24.3

[58] Field of Search ............... 435/6, 91.1, 91.2, 435/172.3, 91.4; 536/22.1, 23.1, 24.3

[56] References Cited

U.S. PATENT DOCUMENTS

| | | | |
|---|---|---|---|
| 4,713,337 | 12/1987 | Jasin et al. | 435/172.3 |
| 4,956,288 | 9/1990 | Barsoum | 435/172.3 |
| 4,959,316 | 9/1990 | Stanislas et al. | 435/172.3 |

FOREIGN PATENT DOCUMENTS

WO 91/06667 of 1991 WIPO.
WO 91.09955 7/1991 WIPO.

OTHER PUBLICATIONS

Hanson et al. (Jan. 1995), "Analysis of biological selections for high-efficiency gene targeting", Mol. Cell. Biol. 15(1):45–51.

Sninsky et al. (1981), "Construction and characterization of a novel two-plasmid system for accomplishing temperature-regulated, amplified expression of cloned adventitious genes in *Escherichia coli*", Gene 16:275–286.

McArthur et al. (1991), "A genetic element that increases the frequency of gene amplification", J. Biol. Chem. 266(9):6000–6005.

Asselbergs et al. (1992), "Endogenous gene and amplifiable cDNA construct both produce unstable t-PA mRNA in Bowes melanoma cells", J. Biotechnol. 23:143–151.

Raibaud et al., Gene, vol. 29, pp. 231–241 (1984).

Kallio et al., Appl Microbiol Biotechnol, vol. 27, pp. 64–71 (1987).

Jannière et al., Gene, vol. 40, pp. 47–55 (1985).

*Primary Examiner*—Stephanie W. Zitomer
*Assistant Examiner*—Jeffrey Fredman
*Attorney, Agent, or Firm*—Steve T. Zelson; Elias J. Lambiris

[57] ABSTRACT

A method of amplifying in vivo a DNA sequence B present in a genome of a parent cell, comprising (a) integrating in a genome of said cell a DNA construct comprising the structure C-M-A-D, in which both A and C denote a DNA sequence which is homologous with a genomic DNA fragment either flanking or overlapping the DNA sequence B, the sequence C being located in the opposite end the sequence B as compared to A, D denotes a DNA sequence which is homologous with a genomic DNA fragment located distal for C as compared to B, and M denotes a DNA sequence encoding a selection marker, (b) selecting for cells in which the DNA sequence M has been integrated in the genome, which cells comprise, in any orientation, the structure A-B-C-M-A-D and (c) propagating the cells selected in step (b) under increasing selection pressure to obtain a cell which has obtained an increased number of genomically integrated copies of the DNA sequences B and M.

19 Claims, 10 Drawing Sheets

Chromosome:

vector + DNA construct:

Integration via C:

Excision via D:

Integration via A:

Excision via D:

Integration via D:

Excision via A:

Excision via C:

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1:

GAATTCTCAT GTTTGACAGC    20

( 2 ) INFORMATION FOR SEQ ID NO:2:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2:

GACTTCTAGA CATATGTAAA TTTCGTTGAT TACATT    36

( 2 ) INFORMATION FOR SEQ ID NO:3:

( i ) SEQUENCE CHARACTERISTICS:
    ( A ) LENGTH: 36 base pairs
    ( B ) TYPE: nucleic acid (C) STRANDEDNESS: single
(D) TOPOLOGY: linear (xi) SEQUENCE DESCRIPTION: SEQ ID NO:3:

GACTGTCCAG AAGCTTAAAA TAAAAAAACG GATTTC    36

(2) INFORMATION FOR SEQ ID NO:4:

(i) SEQUENCE CHARACTERISTICS:
 (A) LENGTH: 20 base pairs
 (B) TYPE: nucleic acid
 (C) STRANDEDNESS: single
 (D) TOPOLOGY: linear (xi) SEQUENCE DESCRIPTION: SEQ ID NO:4:

ATGATACACA GCCGGGGCAA    20

(2) INFORMATION FOR SEQ ID NO:5:

(i) SEQUENCE CHARACTERISTICS:
 (A) LENGTH: 17 base pairs
 (B) TYPE: nucleic acid
 (C) STRANDEDNESS: single
 (D) TOPOLOGY: linear (xi) SEQUENCE DESCRIPTION: SEQ ID NO:5:

GTTGACCAGA CATTACG    17

(2) INFORMATION FOR SEQ ID NO:6:

(i) SEQUENCE CHARACTERISTICS:
 (A) LENGTH: 47 base pairs
 (B) TYPE: nucleic acid
 (C) STRANDEDNESS: single
 (D) TOPOLOGY: linear (xi) SEQUENCE DESCRIPTION: SEQ ID NO:6:

TGAGTCAGCT AGCAACTGTC ATGAAACAAC AAAAACGGCT TTACGCC    47

AMPLIFICATION OF GENOMIC DNA BY SITE SPECIFIC INTEGRATION OF A SELECTABLE MARKER CONSTRUCT

CROSS-REFERENCE TO RELATED APPLICATIONS

This application is a continuation of application Ser. No. 08/432,164, filed May 12, 1996, now abandoned and is a continuation of PCT/DK93/00438 filed Dec. 22, 1993, which is incorporated herein by reference.

FIELD OF THE INVENTION

The present invention relates to a method of amplifying in vivo a DNA sequence present in a genome of a cell, a cell harbouring multiple copies of said amplified DNA sequence in a genome and a vector harbouring a DNA construct to be used in the method. Furthermore, the present invention relates to a method of producing a polypeptide by culturing a cell as described above.

BACKGROUND OF THE INVENTION

A large number of naturally-occurring organisms have been found to produce useful products, the large scale production of which is desirable for research and commercial purposes. Once such product has been identified efforts are being made to develop production methods leading to a high production of the product. One widely used method, which is based on recombinant DNA techniques, is to clone a gene encoding the product, inserting the gene into a suitable expression system permitting the expression of the product and culturing a suitable host cell comprising the expression system, either integrated in the chromosome or as an extrachromosomal entity, under conditions conducive for the expression of the product. However, a prerequisite for using such method is that the gene in question may be identified and cloned, and further that a suitable expression system and host cell for the production are available.

Another approach which may be used for the production of such products is to culture the cell which in nature produces the product or a derivative of such cell under suitable conditions. However, a frequently recognized drawback of such method is that the cell is not a suitable production organism, one reason being that the amount of product produced by such cell is too low to be commercially attractive.

Irrespective of which production method is used, it is normally desirable to be able to increase the production level of a given protein. Thus, efforts are being made to increase the production, e.g. by inserting the gene encoding the product under the control of a strong expression signal, or by increasing the number of copies of the gene in the production organism in question. This latter approach may be accomplished by inserting the gene into a multicopy plasmid which generally, however, tends to be unstable in the host cell in question, or by integrating multiple copies of the gene into the chromosome of the production organism, an approach which generally is considered more attractive because the stability of the construct tend to be higher allowing the gene to be stably maintained in the production organism.

EP 0 284 126 and EP 166 628 disclose methods for stably integrating one or more copies of a gene into the chromosome of a prokaryotic cell already harbouring at least one copy of the gene in question in its chromosome. According to EP 0 284 126, a host cell comprising said gene is transformed with a DNA construct comprising another copy of the gene, whereby, after a suitable selection procedure, a cell is obtained which in its chromosome comprises two copies of the gene separated by an endogenous chromosomal sequence which is vital to the host cell and thereby ensures stable maintenance of the integrated gene. This procedure may be repeated so as to produce cells harbouring multiple copies of the gene in its chromosome.

EP 166 628 relates to a process for amplifying a specific gene in the chromosome of a Bacillus strain thereby obtaining a cell harbouring a so-called "amplifiable unit" comprising the gene, the expression elements of the gene, and a gene encoding a selection marker inserted between two directly repeating sequences termed "duplicated sequences". The gene is introduced into the cell by a plasmid integration vector which is integrated in the Bacillus chromosome and which harbours a marker gene, the gene to be amplified, and one of the duplicated sequences, the other being present on the chromosome of the Bacillus cell.

Both of the above described methods require that the entire gene to be amplified is insertable into the vector to be used in the amplification method and thus, are applicable only when the gene to be amplified is isolated and available on a vector to be used in the method.

BRIEF DISCLOSURE OF THE INVENTION

The present invention relates to a generally novel method of amplifying a DNA sequence present on a genome of the cell, which as compared to the above described methods, has the advantage that there is no requirement that the DNA sequence to be amplified is available in its entirety.

More specifically, in a first aspect the present invention relates to a method of amplifying in vivo a DNA sequence B present in a genome of a parent cell, which method comprises a) integrating in a genome of said cell a DNA construct comprising the structure C-M-A-D, in which A denotes a DNA sequence which is homologous with a genomic DNA fragment either flanking or overlapping the DNA sequence B to be amplified or being a subsequence of the DNA sequence B constituting one of the ends of said sequence B, C denotes a DNA sequence which is homologous with a genomic DNA fragment either flanking or overlapping the DNA sequence B to be amplified or being a subsequence of the DNA sequence B constituting one of the ends of said sequence B, the sequence C being located in the opposite end of the sequence B as compared to A, D denotes a DNA sequence which is homologous with a genomic DNA fragment located distal for C as compared to B, and M denotes a DNA sequence encoding a selection marker, b) selecting for cells in which the DNA sequence M has been integrated in the genome either upstream or downstream of the DNA sequence B together with the sequence A, which cells comprise, in any orientation, the structure A-B-C-M-A-D, and c) propagating the cells selected in step b) under increasing selection pressure for the selection marker encoded by the DNA sequence M so as to obtain a cell which has obtained an increased number of genomic integrated copies of the DNA sequences B and M as compared to the parent cell.

Integration of the DNA construct comprising the structure C-M-A-D into a genome of the parent cell results in a genomic structure in which the DNA sequence B together with a suitable selectable marker is located between two directly repeated DNA sequences A, one of which originates from the genome in question and one from the DNA construct. When a strain comprising such structure is propagated under increasing selection pressure for the marker, the culture is enriched for cells containing duplications, triplications, and higher amplifications of the genes between the two directly repeated sequences. Thus, it is contemplated that the number of copies of the DNA sequence of interest may constitute, 20, 50, 100 or more the upper limit being the number of copies which become a too heavy burden for the cell. By use of the method of the invention it has been found that the amplified DNA is quite stable in the absence of selection for the marker M.

It will be understood that the amplification method of the invention has the important advantage over the prior art methods that the entire DNA sequence to be amplified does not need to be available for the method to be carried out. Only a part of the DNA sequence or its flanking regions need to be known. This is an advantage in that, although DNA isolation and sequencing methods have been substantially improved during the last decade, it is still laborious to isolate and sequence a DNA sequence of interest and in fact, not always possible.

In the present context, the term "genome" is normally intended to indicate a chromosome of the parent cell. However, the term is also intended to indicate any other genome present in the parent cell, an example of which is a plasmid, for instance a large stable plasmid present in the cell.

The term "homologous" as used about the DNA sequences A, C and D is intended to indicate a degree of identity between any of these sequences and the corresponding parts of the genome, which is sufficient for homologous recombination to take place. Preferably, the DNA sequences show identity or substantial identity for at least 8 consecutive base pairs with the corresponding parts of the genome. However, the DNA sequences may be longer, e.g. comprising up to several thousands nucleotides.

The term "flanking" is intended to indicate that the DNA sequence A or C is homologous with the genomic sequence located up to, but not extending into the DNA sequence B. The term "overlapping" is intended to indicate that the DNA sequence A or C is homologous to a part of the genomic sequence which is constituted by one of the ends of the DNA sequence B and the sequence immediately outside this sequence.

The term "located distal for C" as used about the DNA sequence D is intended to be understood in its conventional meaning, i.e. that the DNA sequence D is homologous with a genomic sequence located on the side of the genomic sequence homologous to the DNA sequence C which is opposite to the position of the DNA sequence B to be amplified. The distance between the genomic sequences homologous with the DNA sequences C and D may vary from the situation where C and D are identical or partly overlapping to a separation of several thousand basepairs. However, the DNA sequences between C and D will eventually become deleted from the genome when the method of the invention is carried out.

In another aspect the present invention relates to a cell comprising multiple copies of a DNA sequence comprising the structure M-B in its genome, in which M denotes a DNA sequence encoding a selection marker and B denotes a DNA sequence encoding a desirable polypeptide, the multiple copies of the structure M-B being located between two directly repeated sequences.

In further aspects the invention relates to a DNA construct comprising the structure C-M-A-D and intended for use in the amplification of a genomic DNA sequence B, in which A, C, M, D has the meaning indicated above, as well as a vector harbouring the DNA construct.

Finally, the invention relates to a process for producing a polypeptide encoded by a DNA sequence B comprising culturing a cell as defined above having integrated multiple copies of the DNA sequence B under conditions conducive to the production of the polypeptide and recovering the resulting polypeptide from the culture.

DETAILED DESCRIPTION OF THE INVENTION

Figure 1:
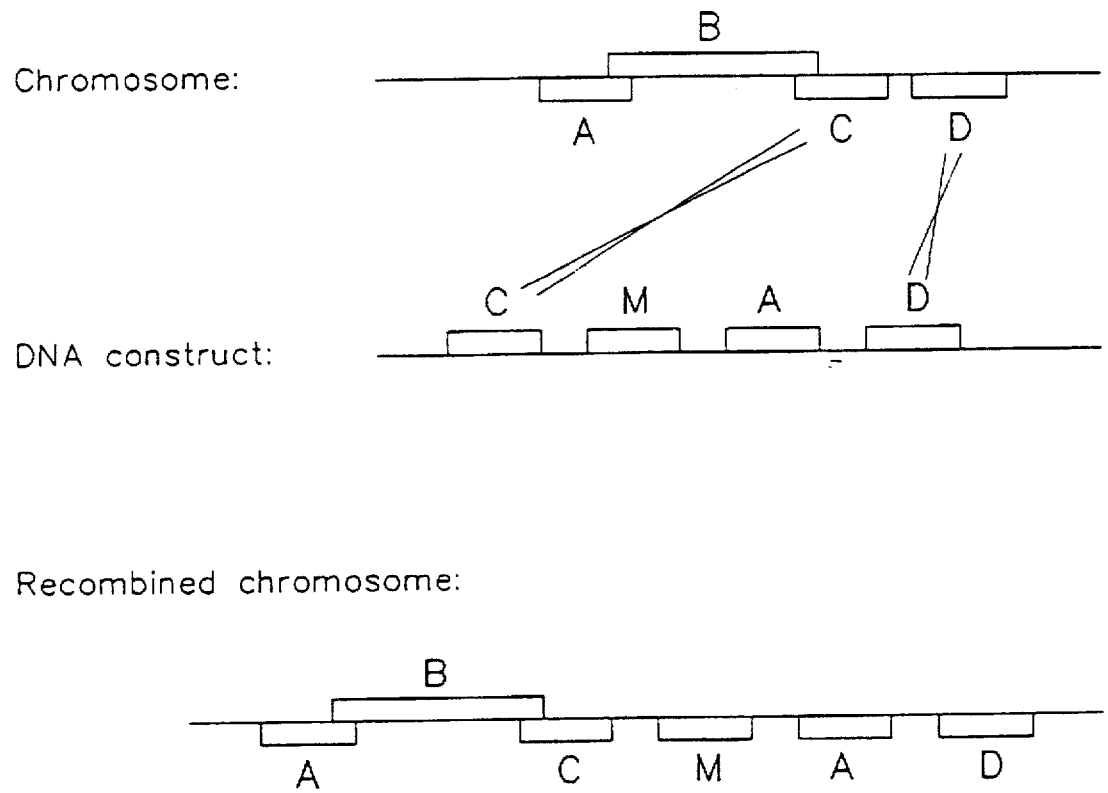

The integration step a) of the method of the invention may be accomplished by any suitable method, the nature of which depends on the organism and DNA construct in question. First, the DNA construct must be introduced into the cell. The DNA construct may be introduced as such using techniques known in the art for direct introduction of DNA, e.g. by use of electroporation, transformation of competent cells, protoplast transformation, or ballistic transformation, but is suitably carried on a vector capable of affording integration of the DNA construct into a genome of the cell.

The vector is advantageously a plasmid or a bacteriophage which may be introduced into the parent cell by any technique suited for the vector and parent cell in question, including transformation as above, protoplast fusion, transfection, transduction and conjugation.

Upon introduction into the parent cell the DNA construct optionally in combination with vector-derived DNA is integrated into a genome by homologous recombination which takes place between the homologous sequences. In the appended FIG. 1 it is illustrated how a double recombination event between a genome and the DNA construct can give rise to a cell according to the invention, containing the structure A-B-C-M-A-D in its genome.

When a vector is used for the integration of the DNA construct, a selection for cells having received the vector may be performed prior to the selection step b) of the method of the invention thereby improving the efficiency with which the integration of the DNA construct takes place. For this purpose, a vector which is able to replicate under certain (permissive) conditions and unable to replicate under other (non-permissive) conditions may be used. The vector may, for instance, be one which is temperature-sensitive for replication. Thus, the vector may be one which is unable to replicate at increased temperatures, which yet permit growth of the parent cell. The cells are initially cultured at a temperature permitting plasmid replication and subsequently after integration into the bacterial genome may have taken place, cultured at a temperature which does not permit plasmid replication so that the vector is lost from the cells unless integrated into the genome.

The vector may further comprise a selectable marker. In this case, the cultivation at the non-permissive temperature may be conducted under selective conditions to ensure that only cells containing the integrated vector which includes the DNA construct and the selectable marker, will survive.

The selectable marker may be any marker known in the art, for instance a gene coding for a product which confers antibiotic resistance to the cell, which confers prototrophy to an auxotrophic strain, or which complements a defect of the host, (e.g. dal genes introduced in a dal strain; cf. B. Diderichsen (1986). Cells surviving under these conditions will be cells containing the vector or cells in which the vector comprising the DNA construct of the invention has been integrated. The selectable marker may, e.g., be excised from a known source or present on a vector, e.g. a plasmid, used for the construction of the DNA construct to be used in the method of the invention.

In the selection step b) of the method of the invention, selection for cells comprising the structure A-B-C-M-A-D, in any orientation, are made. Such cells could be the result of a single recombination event, in which case the vector is still present in the genome, or could advantageously be the result of a double recombination event in which case the vector is not present in the genome. The double recombination event can be the result of two sequential single recombination events, the first consisting of an integration into the genome of the vector containing the structure C-M-A-D, the second consisting of excision of the vector from the genome. The process is illustrated schematically in FIG. 2, from which it is apparent that integration via fragment C followed by excision via fragment D, or vice versa, will give a genome containing the structure A-B-C-M-A-D of the invention.

This selection may be accomplished by growing the cells under selection pressure for the selection marker encoded by the DNA sequence M and analysing the thereby selected cells for the presence of the structure A-B-C-M-A-D, e.g. by use of conventional DNA analysis techniques, including restriction enzyme digestion and gel analysis combined with Southern blotting, or by use of PCR using suitable primers corresponding to characteristic parts of the structure A-B-C-M-A-D.

In one particular embodiment of the invention, a temperature-sensitive vector is used, which in addition to the structure C-M-A-D carries another selectable marker, Y. The vector is introduced into the parent cell at permissive temperature, selecting for either M or Y or both. Propagation is then continued at a non-permissive temperature, and selection for either M or Y or both is maintained. Cells growing under these conditions will have the vector integrated into a genome (by either of the three fragments C, A or D). Subsequently, cells are grown at a permissive temperature in the absence of selection pressure. This will allow plasmid replication, excision of the integrated plasmid from the genome (again by any of the three fragments C, A or D), and eventually loss of plasmid from the cells. Cells are now selected, which still contain the selection marker M, and such cells screened for the presence of the selection marker Y, e.g. by replica plating. Such cells can only arise by integration via fragment C followed by excision via fragment D, or vice versa, and contain the structure A-B-C-M-A-D in a genome.

The DNA sequence M present in the DNA construct to be integrated by the present method may encode any selectable marker, e.g. of any type as described above in connection with the marker optionally carried by the vector to be used in the method of the invention. Thus, the DNA sequence M may encode an antibiotic resistance such as resistance to kanamycin, tetracyclin, ampicillin, erythromycin, chloramphenicol, or a resistance to various heavy metals such as selenate, antimony or arsenate.

It will be understood that the increased number of genomically integrated copies of the DNA sequences B and M obtained in the propagation step c) of the method of the invention is the result of successive recombination events between initially the two copies of the DNA sequence A (directly repeated) surrounding the DNA sequences B and M. It may be possible to control the amplification of the DNA sequence B and thus arrive at a predetermined number of copies in terms of the selectable marker used and the strength of the selection pressure used in the propagation step c). There is no theoretical upper limit for the number of copies of the DNA sequences B and M to be obtained in this step, but in practice the number of copies will be limited by the burden put on the host cell.

It should be noted that once the DNA construct has been integrated in a genome of the parent cell, this may be cultured in the absence of selection pressure without substantial loss of the DNA construct or parts thereof from the cell. This is believed to be ascribable to the fact that the integrated DNA is incapable of autonomous replication, and is replicated together with the host genome in which it is integrated.

It will be understood that the novel method of the invention is generally applicable for the amplification of a DNA sequence present in a genome irrespective of the type of cell or genome. The only restriction as to the nature of the cell is that the cell is one which may be transformed or which may otherwise allow for introduction of foreign DNA. The cell may comprise one or more genomes, e.g. in the form of plasmids or chromosomes.

For instance, the parent cell may be a microbial cell, an insect cell, a plant cell, a vertebrate cell, or a mammalian cell. When the parent cell is a microbial cell it may be a prokaryotic or a eukaryotic cell such as a bacterial or fungal (including yeast) cell.

When the cell is a bacterial cell it may be a cell of a gram-positive bacterium such as Bacillus, Streptomyces and Pseudomonas, e.g. a cell of *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus thuringiensis, Streptomyces lividans* or *Streptomyces murinus*, or a cell of a gram-negative bacterium such as Escherichia and Pseudomonas. Other examples of bacterial cells include cells of archaebacteria such as Pyrococcus.

When the cell is a fungal cell it may be a yeast cell such as a cell of Saccharomyces or Schizosaccharomyces, or a cell of a filamentous fungus such as a cell of Aspergillus, e.g. *A. niger, A. nidulans* or *A. oryzae*.

The DNA sequence B to be amplified may be native to the parent cell or may alternatively be one which is not native to the parent but which has been cloned from another organism (e.g. of the type described above) or which has been synthesized and subsequently introduced into the host chromosome or another host carried genome by any convenient process, e.g. crossing-over, prior to the integration of the DNA construct of the invention. The DNA sequence B may be introduced in its entirety or may be assembled in the host genome in question, e.g. by successive introduction of constituent sequences of sequence B. This latter approach is of particular use when the DNA sequence B is unclonable in its entirety.

The DNA sequence B may be one having or encoding any function. For instance, the DNA sequence B may comprise an open reading frame, e.g. encoding a structural or regulatory protein or polypeptide, and may be a single gene, a cluster of genes or an operon. The DNA sequence B may further comprise one or more regulatory signals involved in the expression from the open reading frame, such as transcription or translation termination or initiation sequences.

Preferably, the DNA sequence B comprises an expressible gene which may contain all necessary regulatory sequences such as a promoter, a terminator, a ribosome binding site, etc.

Normally, the DNA sequence B to be amplified is one encoding a desirable product such as an enzyme, a hormone, an antigenic component, an immunoactive protein or peptide, a growth factor, an allergen, a tumor associated antigen, a blood protein, and the like, in other words any kind of industrially useful product, the production of which is desirable.

Examples of enzymes of interest include amylolytic, lipolytic and proteolytic enzymes, transferases, isomerases, peroxidases, oxidases etc. In particular it is preferred that the DNA sequence B encodes a protease, a lipase, an amylase, a galactosidase, a pullulanase, a cellulase, a glucose isomerase, a protein disulphide isomerase, a CGT'ase (cyclodextrin gluconotransferase), a glucose oxidase, a glucosyl transferase, or a xylanase.

Examples of other useful products include insulin-like growth factors, insulin, human or bovine growth hormone, human blood coagulation factors, interleukin, tPA etc.

Alternatively, the DNA sequence B may comprise one or more genes encoding a biosynthetic pathway, one or more genes encoding elements of the cells transcription, translation or protein secretion apparatus (for instance sigma factors or sec genes of procaryotic cells), a regulatory factor acting in the cell or a metal resistance, or the DNA sequence B may complement an auxotrophic mutation of the parent cell.

From the above disclosure it will be understood that the DNA sequences A and C may be homologous with any genomic sequence overlapping or flanking the DNA sequence B. When the DNA sequence B is a gene, the DNA sequence A or C may advantageously be homologous to a full or partial promoter sequence upstream of the coding part of the DNA sequence B. An example of such construct is shown in Example 1 hereinafter.

The DNA construct used in the method of the invention may be synthesized through a series of genetic manipulations employing methods and enzymes known in the art. Typically, each of genomic sequences with which the DNA sequences A, C and D are to be homologous are identified by conventional DNA analysis methods.

For instance, a cDNA or genomic library may be prepared from the organism in question and the DNA sequence B to be amplified identified therein. When at least a part of the DNA sequence B is known, the DNA sequence B may be identified by screening for positive clones by conventional hybridization procedures, e.g. using oligonucleotide probes synthesized on the part of the DNA sequence B in accordance with standard techniques (cf. Sambrook et al., 1989), or more preferably, by use of polymerase chain reaction (PCR) using degenerate oligonucleotide probes prepared on the basis of the known part of the DNA sequence B. For instance, the PCR may be carried out using the techniques described in U.S. Pat. No. 4,683,202 or by R. K. Saiki et al. (1988).

When the nucleotide sequence of the DNA sequence B is unknown, and an expression product thereof is known, one may screen cDNA or genomic clones for an activity of the product and thereby identify a clone from which the activity is expressed. Subsequently, part of the DNA of the clone is isolated and sequenced and the location of the DNA sequence B or part thereof is identified.

The DNA sequence B to be amplified may be identified by way of mutation, e.g. by transposon insertions that destroy the cell's ability to produce the product of B, and parts of the DNA sequence of B may be determined e.g. by inverse PCR using primers corresponding to the transposon sequences. In this way, the DNA sequences comprising the ends of B and flanking regions may be determined, even if B may not be clonable either partly or in its entirety.

In order to be able to prepare the DNA sequences A, C and D at least the 5' and 3' ends of B (including at least sufficient sequence data to allow specific binding of a probe or PCR primer, e. g. 12 nucleotides) should be known. Once the sequences of these ends have been identified, the DNA sequences flanking or overlapping both ends of the DNA sequence B may be identified, e.g. by hybridization or PCR analysis and subsequently sequenced. On the basis of these sequences the DNA sequences A, C and D are prepared.

The DNA A, C, D and M may be prepared synthetically or may be of cDNA or genomic origin, e.g. isolated from a genomic or cDNA library by use of the above described methods.

Alternatively, the DNA sequence of the DNA construct of the invention may be prepared synthetically by established standard methods, e.g. the phosphoamidite method described by Beaucage and Caruthers (1981), or the method described by Matthes et al. (1984). According to the phosphoamidite method, oligonucleotides are synthesized, e.g. in an automatic DNA synthesizer, purified, annealed, ligated and cloned in appropriate vectors.

Finally, the DNA construct may be of mixed genomic and synthetic, mixed synthetic and cDNA or mixed genomic and cDNA origin prepared by ligating fragments of synthetic, genomic or cDNA origin (as appropriate), the fragments corresponding to various parts of the entire recombinant DNA molecule, in accordance with standard techniques.

As indicated above, the DNA sequence B is advantageously one which codes for a polypeptide of interest, and the present invention consequently further relates to a process for producing a polypeptide of interest, comprising culturing a cell according to the invention containing multiple copies of a DNA sequence comprising the structure M-B in a genome, in which B encodes the polypeptide of interest, under conditions conducive to the production of the polypeptide and recovering the resulting polypeptide from the culture. The polypeptide produced by the present process may be any of the products listed above such as an enzyme, e.g. a protease, amylase or lipase.

The present invention is further illustrated in the appended drawing in which

Figure 2:
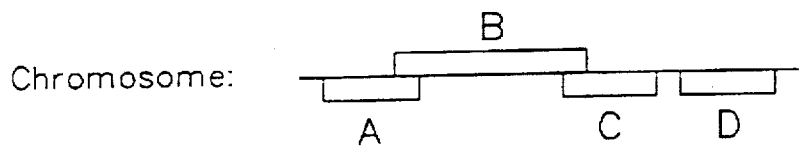
Figure 2:
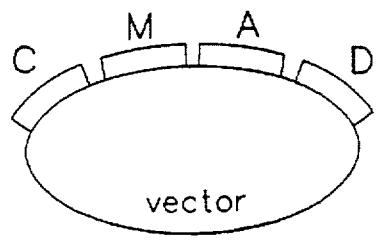
Figure 2:
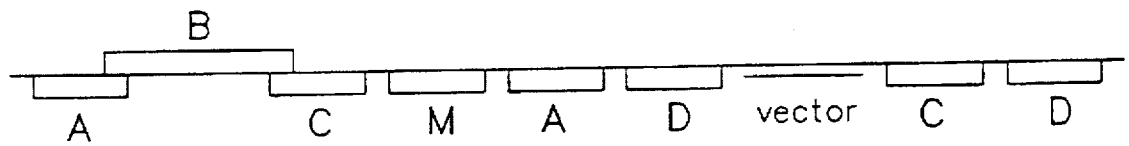
Figure 2:
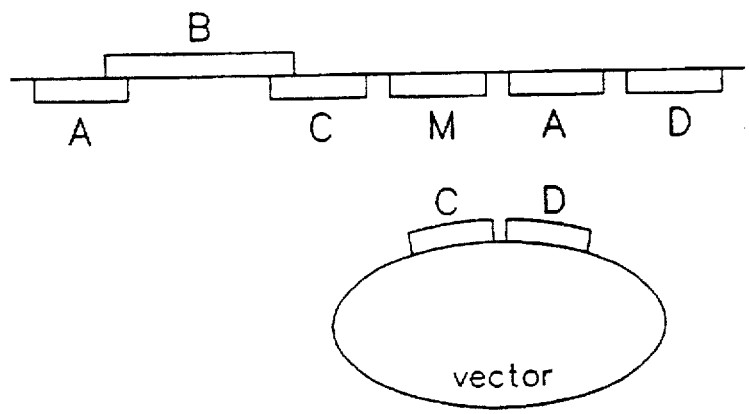
Figure 2:
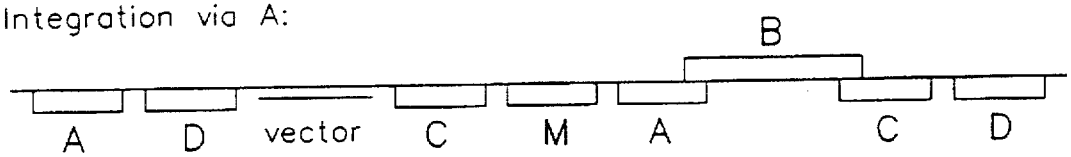
Figure 2:
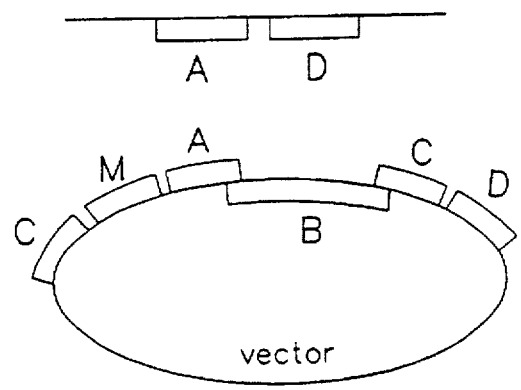
Figure 2:
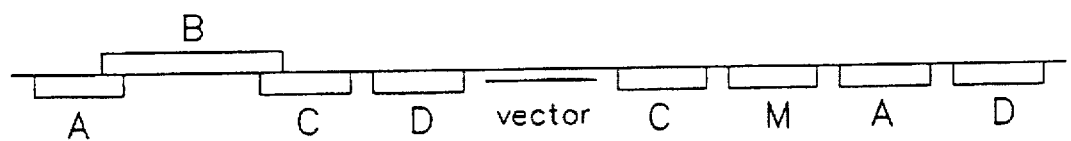
Figure 2:
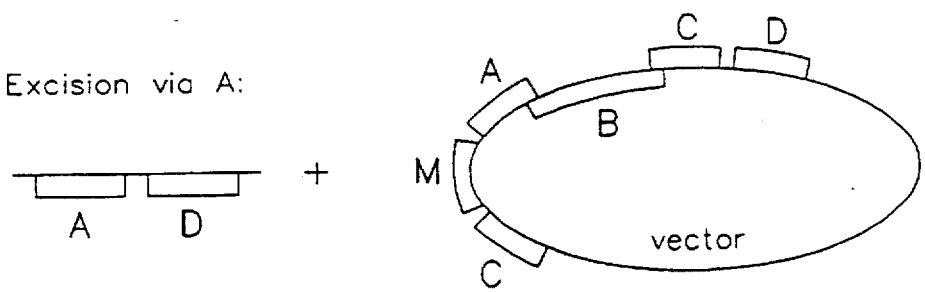
Figure 2:
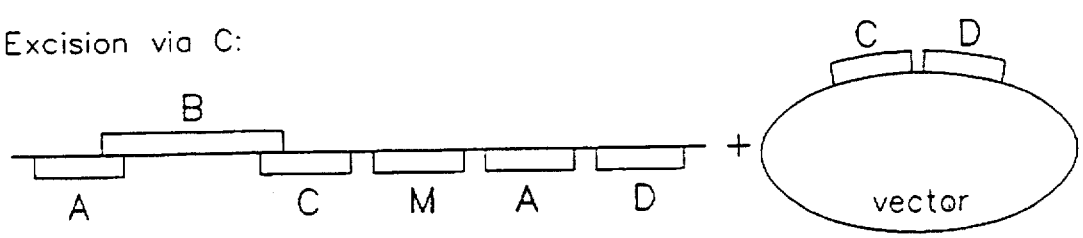
Figure 3:
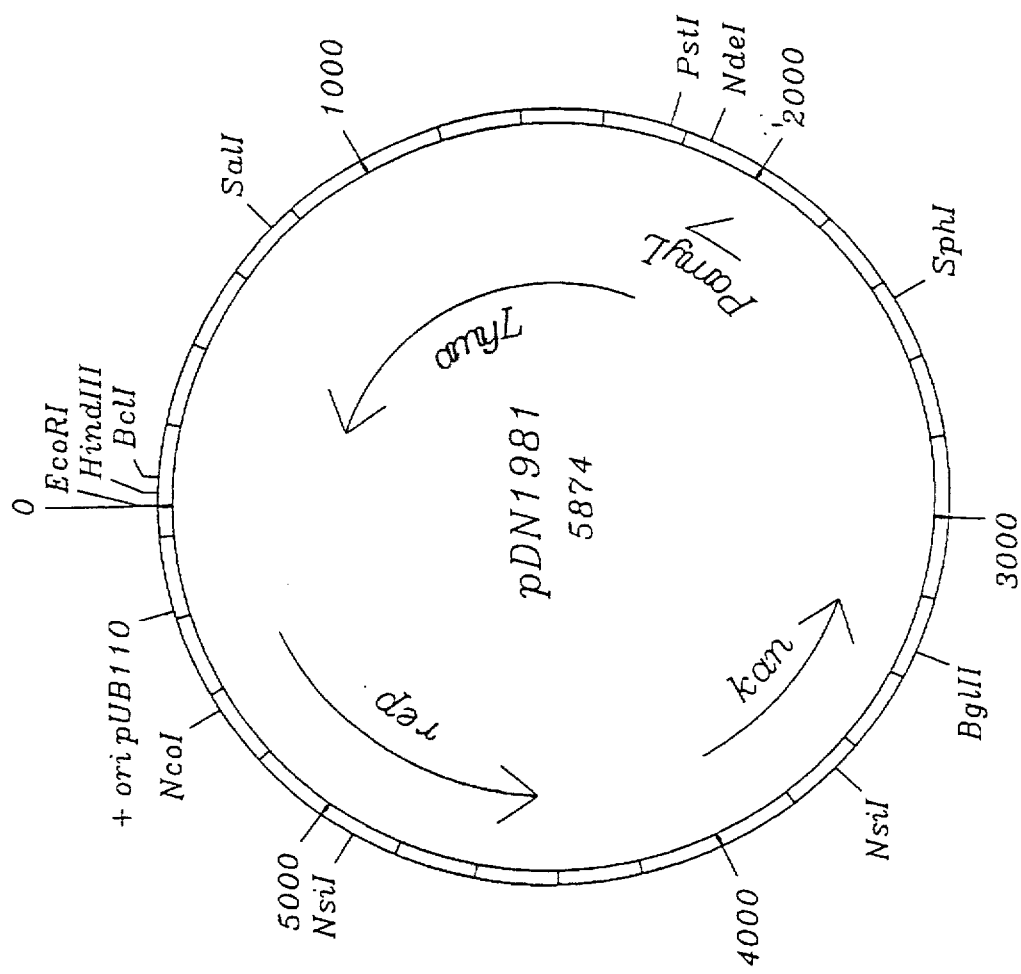
Figure 4:
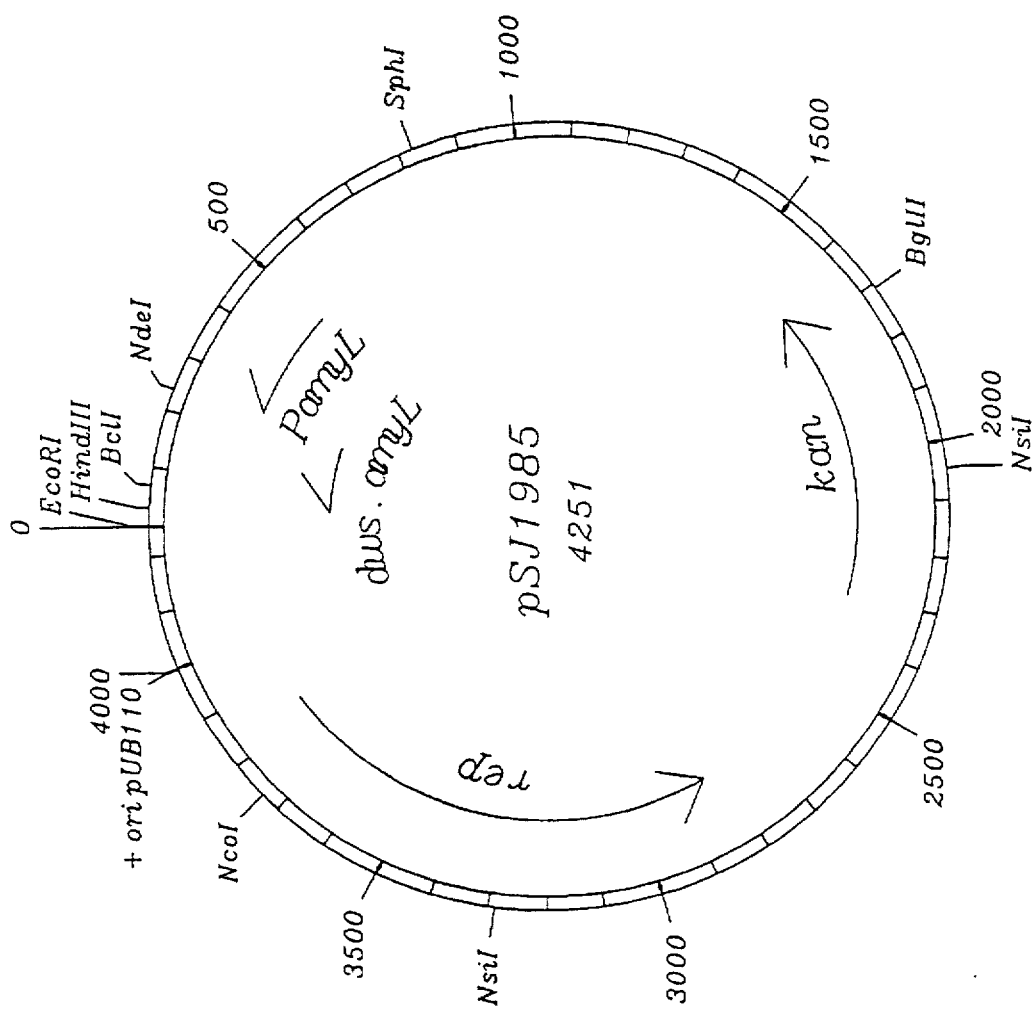
Figure 5:
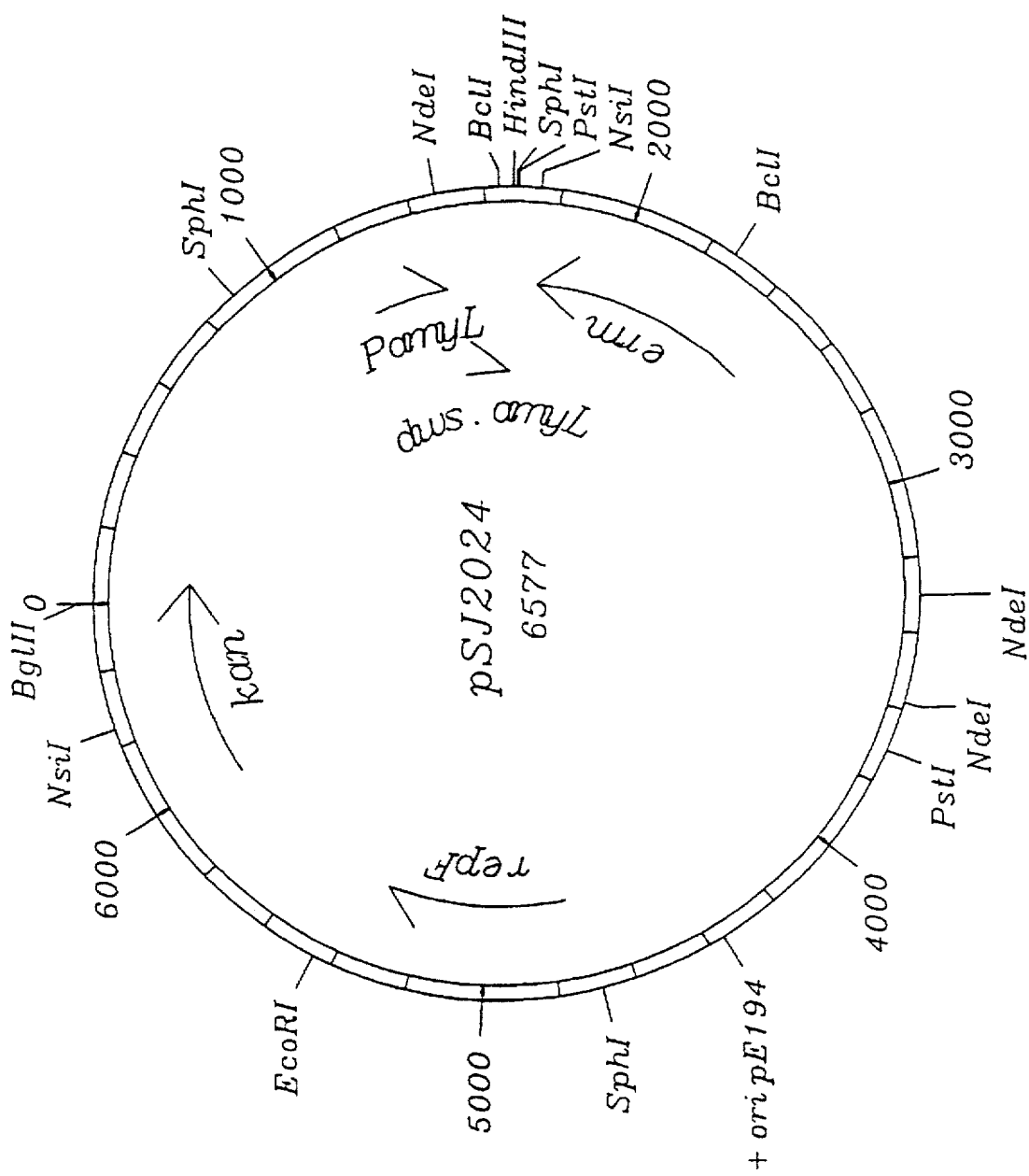
Figure 6:
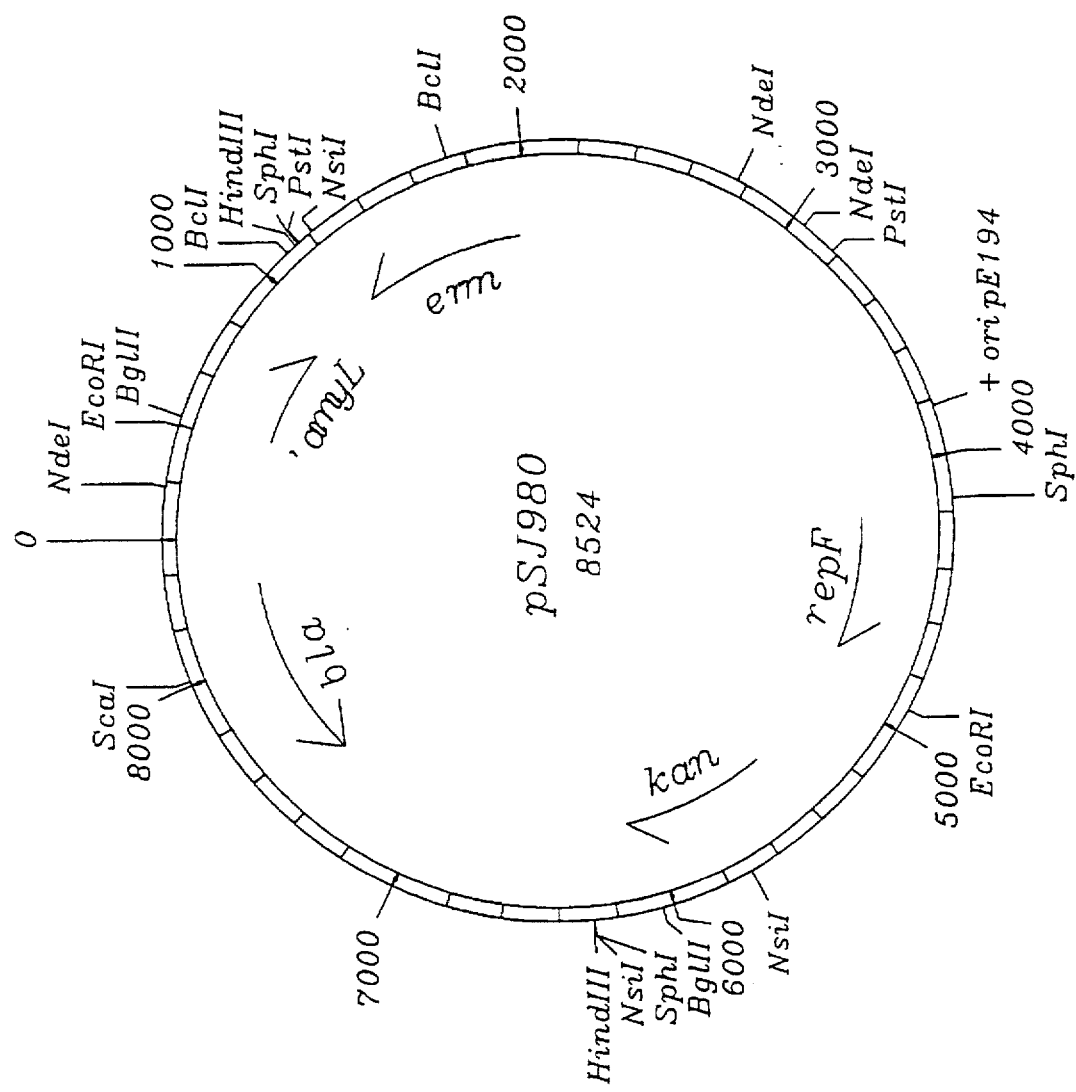
Figure 7:
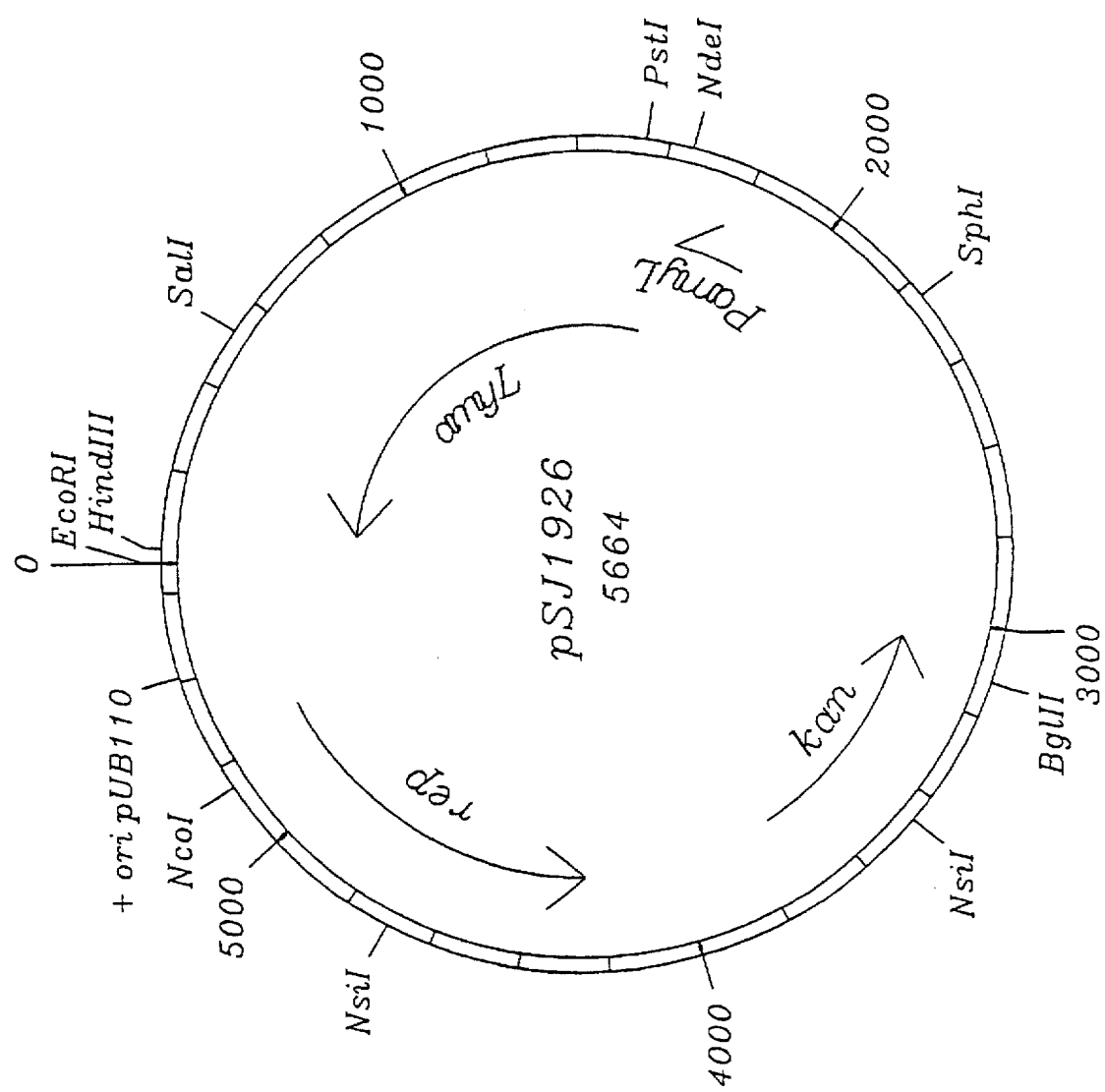
Figure 8:
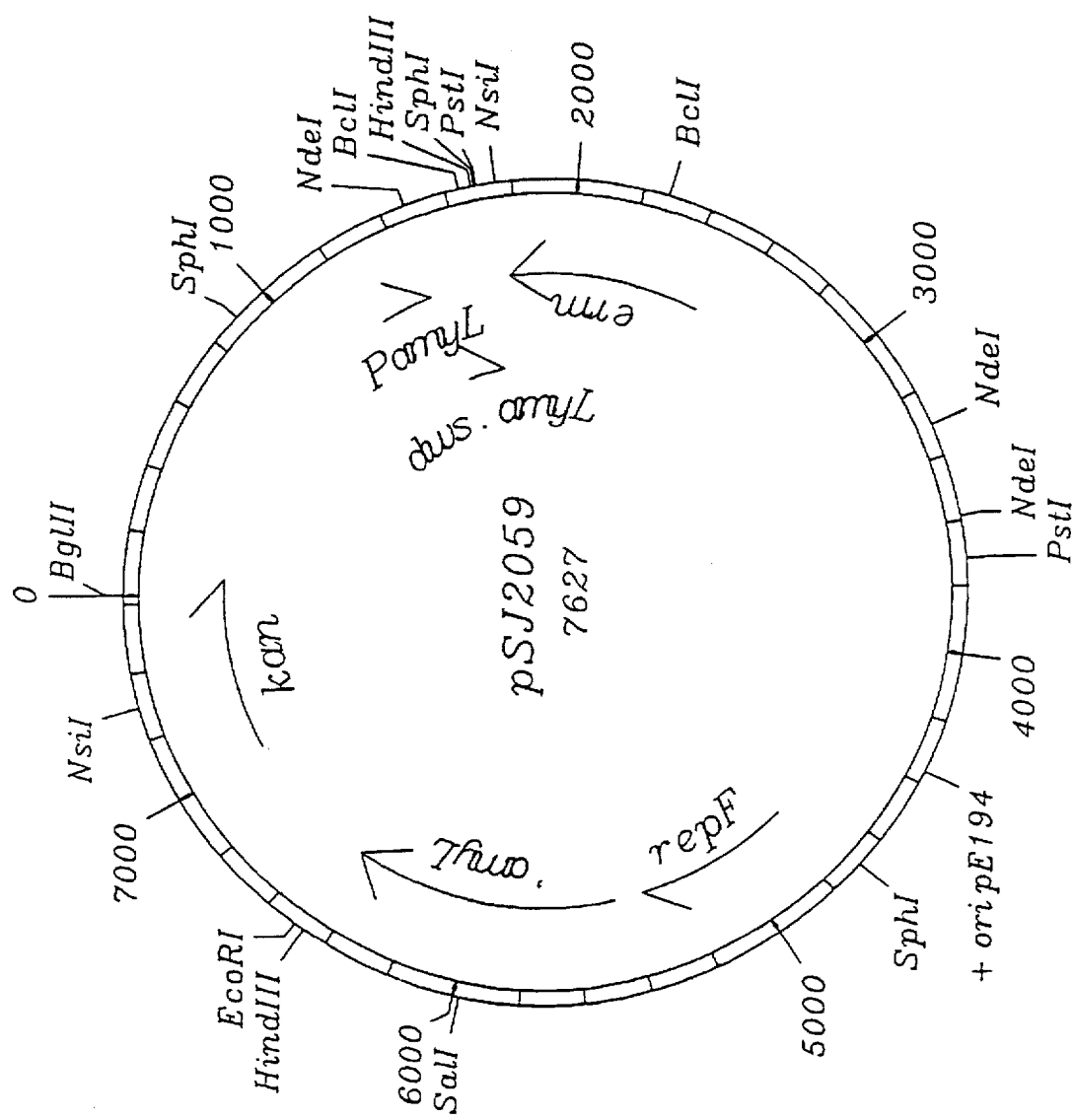
Figure 9:
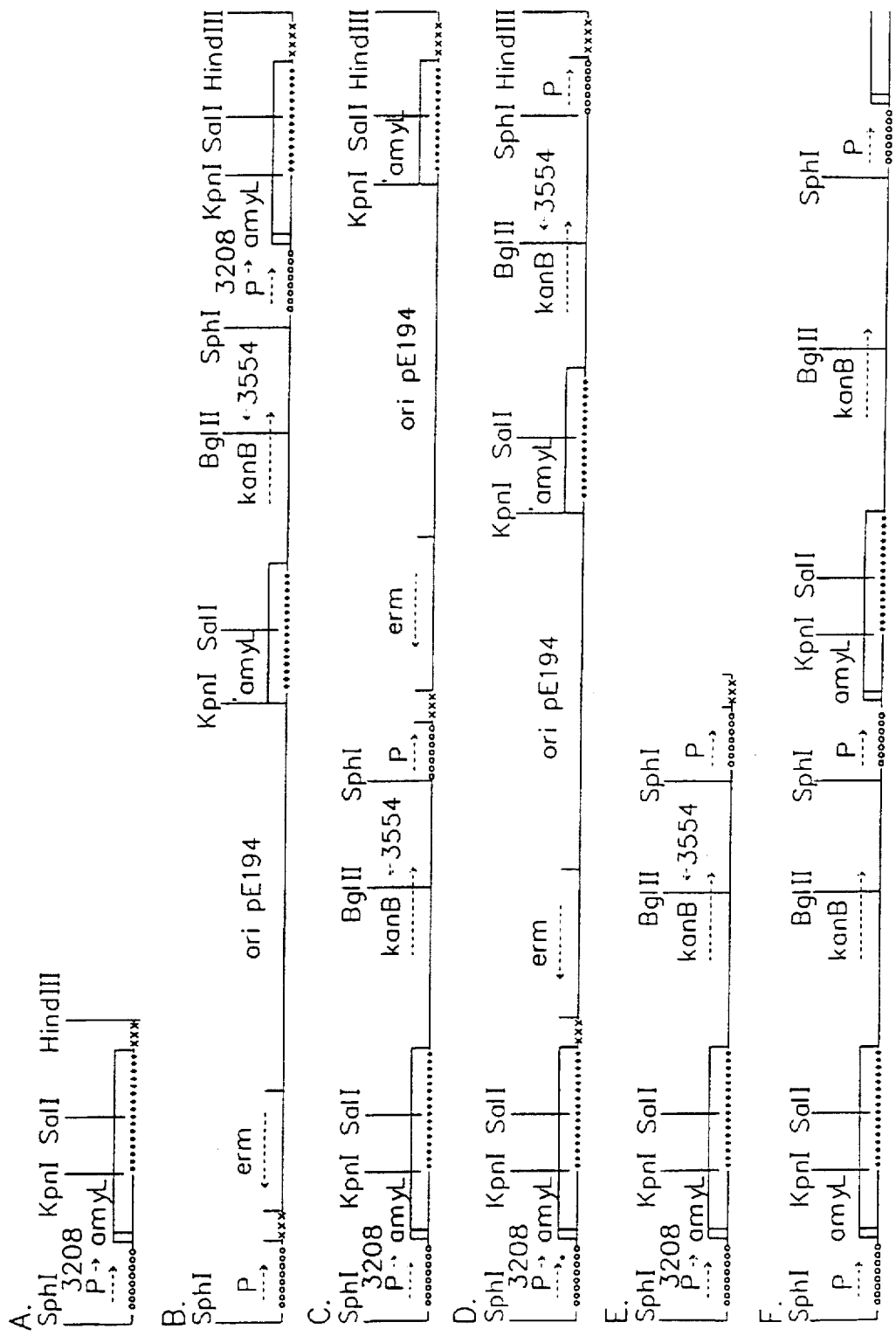

FIG. 1 illustrates a double recombination event between a genome and a DNA construct of the invention which results in a cell containing the structure A-B-C-M-A-D in its genome, FIG. 2 illustrates a double recombination event which is the result of two sequential single recombination events, the first consisting of an integration into the genome of the vector containing the structure C-M-A-D, the second consisting of excision of the vector from the genome, resulting in a genome containing the structure A-B-C-M-A-D of the invention. Various possibilities of integration and excision, respectively, are illustrated, FIG. 3 is a restriction map of plasmid pDN1981, FIG. 4 is a restriction map of plasmid pSJ1985, FIG. 5 is a restriction map of plasmid pSJ2024, FIG. 6 is a restriction map of plasmid pSJ980, FIG. 7 is a restriction map of plasmid pSJ1926, FIG. 8 is a restriction map of plasmid pSJ2059, and FIG. 9 illustrates genomic maps and integration events referred to in Example 1, of which A illustrates the amyL gene in the *B. licheniformis* chromosome, B integration via promoter fragment (ooooooo), C integration via 'amyL fragment (the 5' part of the coding sequence **********), D integration via the downstream amyL fragment (downstream of the coding sequence xxxx), E excision of plasmid from integrant type C via the homology downstream of the coding sequence (xxx), F amplification of the P-amyL-kanB region (initially via the two promoter regions oooooo).

The invention is further illustrated in the following examples which is not, in any manner, intended to limit the scope of the invention as claimed.

MATERIALS AND METHODS

Strains

*Bacillus licheniformis* SJ1904 is the α-amylase producing strain derived from strain SJ1707 by integration/excision of plasmid pSJ1755 as described in example 6 of WO 93/10249, the contents of which is incorporated herein by reference.

*Bacillus subtilis* DN1885: an amyE, amyR2, spo$^+$, Pro$^+$ derivative of *B.subtilis* 168, (Diderichsen et al., 1990).

| Media: | | |
|---|---|---|
| TY: | Trypticase | 20 g/l |
| | Yeast extract | 5 g/l |
| | FeCl$_2$.4H$_2$O | 6 mg/l |
| | MnCl$_2$.4H$_2$O | 1 mg/l |
| | MgSO$_4$.7H$_2$O | 15 mg/l |
| | pH | 7.3 |
| BPX: | Potato starch | 100 g/l |
| | Barley flour | 50 g/l |
| | BAN 5000 SKB | 0.1 g/l |
| | Sodium caseinate | 10 g/l |
| | Soy Bean Meal | 20 g/l |
| | Na$_2$HPO$_4$, 12 H$_2$O | 9 g/l |
| | Pluronic | 0.1 g/l |
| LB agar: | Bacto-tryptone | 10 g/l |
| | Bacto yeast extract | 5 g/l |
| | NaCl | 10 g/l |
| | Bacto agar | 15 g/l |
| | Adjusted to pH 7.5 with NaOH | |

GENERAL METHODS

The experimental techniques used to construct the plasmids were standard techniques within the field of recombinant DNA technology, cf. Sambrook et al. (1989).

Restriction endonucleases were purchased from New England Biolabs and Boehringer Mannheim and used as recommended by the manufacturers. T4 DNA ligase was purchased from New England Biolabs and used as recommended by the manufacturer.

Preparation of plasmid DNA from all strains was conducted by the method described by Kieser, 1984.

Transformation of *B. subtilis*

Competent cells were prepared and transformed as described by Yasbin et al., 1975.

Transformation of *B. licheniformis*

Plasmids were introduced into *B. licheniformis* by polyethylene glycol-mediated protoplast transformation described by Akamatzu, 1984.

Amylase activity was determined with the Phadebas® Amylase Test kit from Pharmacia Diagnostics as described by the supplier.

EXAMPLES

EXAMPLE 1

Amplification of an Amylase Coding Gene

This example illustrates the amplification of an amylase coding gene present in the chromosome of the *B. licheniformis* strain SJ1904. The strain constructed according to this example is one, which in its chromosome in the following order contain:

1) The amylase promoter, 2) The amylase structural gene, 3) a kanamycin resistance gene, and 4) another copy of the amylase promoter. The two copies of the amylase promoter in this case functions as the directly repeated DNA sequences A.

Selection for growth at increasing levels of kanamycin is shown to lead to amplification of the amylase-coding gene (including promoter) and the kanamycin resistance gene.

Plasmid Constructions

All plasmids were constructed in *B. subtilis* DN1885, selecting for kanamycin resistance (10 μg/ml).

pDN1981 (FIG. 3) contains the *B. licheniformis* α-amylase (amyL) gene and has been described by Jørgensen et al., 1990.

pSJ1985 (FIG. 4) contains the amyL promoter (P$_{amyL}$), followed by a 210 bp fragment which originally was situated immediately downstream of the amyL terminator sequence. The fragment was PCR amplified from pDN1981 with primers LWN3226+LWN3223 (Table 1), digested with NdeI and HindIII, and ligated to the 4 kb NdeI-HindIII fragment from pDN1981 to give pSJ1985.

pSJ2024 (FIG. 5) contains this combination of promoter and downstream fragment on a temperature-sensitive plasmid based on pE194 (Horinouchi and Weisblum, 1982b). It was constructed by ligation of the 1.7 kb BglII-HindIII fragment from pSJ1985 to the 4.9 kb BglII-HindIII fragment of pSJ980 (FIG. 6). pSJ980 is described in WO 93/10249.

pSJ1926 (FIG. 7) contains the amyL gene including its terminator sequence, but has been deleted of the sequences downstream of the terminator (the downstream 210 bp fragment contained on pSJ1985 is thus not present on pSJ1926). A 0.5 kb fragment from pDN1981 was PCR amplified with primers LWN3224+LWN3227 (Table I), digested with SalI and HindIII, and ligated to the 5.2 kb SalI-HindIII fragment from pDN1981, giving pSJ1926. The SalI-HindIII fragment of pSJ1926 derived by PCR amplification has been DNA sequenced and contains no PCR induced mutations.

pSJ2059 (FIG. 8) contains a 1 kb fragment of the amyL gene just including the terminator sequence, a kanamycin resistance gene, the amyL promoter, and finally the fragment downstream from the amyL terminator, all on a temperature-sensitive origin. pSJ1926 was digested with EcoRI and KpnI, and the 1 kb fragment inserted between EcoRI and KpnI in pSJ2024, to give pSJ2059.

TABLE 1

List of primers

<EcoRI>
LWN3223: 5'-GAA TTC TCA TGT TTG ACA GC -3' (SEQ ID #1)
pos. 1–20 in pDN1981v2 sequence
<–XBaI–><–NdeI–>

TABLE 1-continued

List of primers

LWN3226: 5'-GAC TTC TAG ACA TAT GTA AAT TTC GTT GAT TAC ATT -3' (SEQ ID #2)
    pos. 2221-2240 in amyLv2 sequence
        <HindIII
LWN3227: 5'-GAC TGT CCA GAA GCT TAA AAT AAA AAA ACG GAT TTC -3' (SEQ ID #3)
    pos. 2210-2190 in amyLv2 sequence
LWN3224: 5'-ATG ATA CAC AGC CGG GGC AA -3' (SEQ ID #4)
    pos. 1690-1710 in amyLv2 sequence
LWN3554: 5'-GTT GAC CAG ACA TTA CG -3' (SEQ ID #5)
    pos. 1271-1201 in kanB sequence
        <-NheI->
LWN3208: 5'-TGA GTC AGC TAG CAA CTG TCA TGA AAC AAC AAA AAC GGC TTT ACG CC
    -3' (SEQ ID #6)
    pos. 622-650 in amyLv2 sequence.

Transformation of B. licheniformis pSJ2059 was introduced into B. licheniformis SJ1904 by protoplast transformation, selecting for erythromycin resistance (5 μg/ml). One transformant thus obtained was strain SJ2127.

Integration

SJ2127 was streaked on LB plates with 10 μg/ml kanamycin and incubated at 50° C. As pSJ2059 is temperature-sensitive for replication, only cells containing a chromosomally integrated copy of the plasmid will give rise to colonies.

pSJ2059 contains three different regions of homology to the chromosomal amyL region in SJ1904, and integration is possible by recombination at any of these three regions. This would give strains, in which the chromosome would look as indicated in FIG. 9, B, C or D.

A plasmid integrated as in FIG. 9B would not be able to excise so as to give the wanted strain.

A plasmid integrated as in FIG. 9C could give the wanted strain if excision took place by recombination at the downstream fragment.

A plasmid integrated as in FIG. 9D could give the wanted strain if excision took place by recombination at the amyL structural gene fragment.

8 colonies from the 50° C. plate was checked by PCR amplification, using primers LWN3208+LWN3554 (table I). The reactions were performed directly on material obtained by resuspending and boiling the cells in TY medium. The position of the primers is indicated on FIG. 9, B, D and E.

No PCR amplified fragment should be obtained from a B-type integrant, whereas a C-type should give a 2.7 kb fragment, and a D-type a 7.5 kb fragment.

From 5 of the 8 colonies, a 2.7 kb fragment was observed, indicating that the integration in these cases had taken place via the amyL structural gene fragment, giving the C-type of integrants. These were then propagated in TY medium at 30° C., to allow excision and loss of the plasmid. Following three transfers in TY medium, Kana$^R$ Erm$^S$ colonies were found by replica plating. The erythromycin sensitivity indicates loss of the plasmid. The 2.7 kb fragment could still be produced by PCR amplification from these colonies, as expected if excision had taken place by recombination at the downstream fragment, giving the result shown in FIG. 9E. One strain obtained from each of the 5 individual 50° C. colonies were kept, as SJ2147-2151.

Amplification

The α-amylase (amyL)+kanamycin resistance genes in strains SJ2148 and SJ2150 were amplified by the following procedure:

The strains were inoculated in 10 ml TY medium+10 μg/ml kanamycin and shaken at 37° C. overnight. New 10 ml cultures containing 20, 50, 100, and 200 μg/ml kanamycin were inoculated with 100 μl of the 10 μg/ml culture, and shaken at 37° C. overnight. 10 ml cultures containing 500, 1000, 1500, 2000, and 2500 μg/ml kanamycin were inoculated with 100 μl of the 200 μg/ml culture.

The 2000 and the 2500 μg/ml cultures were incubated for 4 days, the others harvested after overnight growth. Aliquots of all cultures were frozen in 15% glycerol, and cells harvested for preparation of chromosomal DNA.

| Strains isolated | | |
|---|---|---|
| Mother strain: Kanamycin concentration μg/ml | SJ2148 | SJ2150 |
| 10 | SJ2172 | SJ2182 |
| 20 | SJ2173 | SJ2183 |
| 50 | SJ2174 | SJ2184 |
| 100 | SJ2175 | SJ2185 |
| 200 | SJ2176 | SJ2186 |
| 500 | SJ2177 | SJ2187 |
| 1000 | SJ2178 | SJ2188 |
| 1500 | SJ2179 | SJ2189 |
| 2000 | SJ2180 | SJ2190 |
| 2500 | SJ2181 | SJ2191 |

Chromosomal DNA from the above strains was digested with BglII, which should give a 4.1 kb fragment derived from the amplified DNA (see FIG. 9F). This fragment is visible in an EtBr-stained gel even in the strains selected at 10 μg/ml kanamycin, becomes increasingly conspicuous at 20 and 50 μg/ml, and stays at the high level in the rest of the strains.

Yield Effect of Amplification

Shake flasks with BPX medium were inoculated directly from the glycerol-frozen cultures, and shaken at 300 rpm at 37° C.

The α-amylase yields obtained with the amplified strains were compared to the yield obtained with strain SJ1904.

| | Experiment A | | Experiment B | |
|---|---|---|---|---|
| Strain | Kanamycin in shake flask μg/ml | 7 days Rel. Yield | 4 days Rel. Yield | 6 days Rel. Yield |
| SJ2172 | 10 | 2.76 | | |
| | 0 | 2.6 | | |
| SJ2173 | 20 | 3.44 | | |
| | 0 | 3.04 | 1.92 | 2.72 |

-continued

| | Experiment A | | Experiment B | |
|---|---|---|---|---|
| | Kanamycin in shake | | | |
| Strain | flask µg/ml | 7 days Rel. Yield | 4 days Rel. Yield | 6 days Rel. Yield |
| SJ2174 | 50 | 2.68 | | |
| | 0 | 2.72 | | |
| SJ2175 | 100 | 3.24 | | |
| | 0 | 2.84 | 1.84 | 2.88 |
| SJ2176 | 200 | 3.2 | | |
| | 0 | 3.24 | 1.84 | 2.84 |
| SJ2177 | 500 | 0.72 | | |
| | 0 | 3.24 | 1.76 | 2.76 |
| SJ2182 | 10 | 0.48 | | |
| | 0 | 2.0 | | |
| SJ2183 | 20 | 3.68 | | |
| | 0 | 3.68 | 2.04 | 2.6 |
| SJ2184 | 50 | 2.96 | | |
| | 0 | 2.8 | | |
| SJ2185 | 100 | 2.8 | | |
| | 0 | 3.2 | 1.44 | 2.32 |
| SJ2186 | 200 | 2.96 | | |
| | 0 | 2.92 | | |
| SJ2187 | 500 | 0.6 | | |
| | 0 | 3.56 | 1.68 | 2.6 |
| SJ1904 | 0 | 1.00 | 0.6 | 1.00 |

It is apparent that the amplified strains all produce more α-amylase than does the parent strain.

EXAMPLE 2
Amplification of a CGTase Coding Gene

This example illustrates the amplification of a gene coding for a cyclodextrin glycosyltransferase (cgtA). The gene was originally cloned from a Thermoanaerobacter sp. and inserted in one copy into the chromosome of a *Bacillus licheniformis* strain, replacing the endogenous alpha-amylase gene (amyL) of that strain. The CGTase gene was combined with an efficient mutant version of the alpha-amylase promoter and the alpha-amylase signal peptide on the plasmid used in this process, and transformation of *B. licheniformis* with the recombinant construct was only succesful when a spontaneous recombination event transferred the amyL-cgtA gene to the chromosome under control of the wild-type amyL promoter. A later recombination step was then used to introduce the mutant promoter in front of the chromosomal amyL-cgtA gene. This work, resulting among others in strain SJ1707 used in the present example, has been described in WO 93/10249 and WO 93/10248.

As the inventor was unable to obtain transformants of *B. licheniformis* with plasmids containing the amyL-cgtA gene expressed from the mutant promoter, amplification of this expression cassette in the chromosome was not possible by methods which required the introduction of the entire cassette in one step, but was possible by the method described in the present invention.

The strain constructed according to this example is one, which in its chromosome in the following order contain:

1) The mutant amyL promoter, 2) the amyL-cgtA gene, 3) a kanamycin resistance gene, and 4) another copy of the mutant amyL promoter. The two copies of the amyL promoter in this case functions as the directly repeated DNA sequences A.

Selection for growth at increasing levels of kanamycin is shown to lead to amplification of the amyL-cgtA gene, including the mutant promoter, and the kanamycin resistance gene.

The chromosome of SJ1707 contains a fragment of the amyL gene distal to the amyL-cgtA construct (see WO 93/10249). Plasmid pSJ2059 could therefore be used as a tool to construct an amplifiable derivative of strain SJ1707 in the same manner as it was used in example 1 for amplification of the amylase gene of *B. licheniformis*.

Transformation pSJ2059 was introduced into *B. licheniformis* SJ1707 by protoplast transformation, selecting for erythromycin resistance (5 µg/ml) at 30° C.

One transformant obtained was kept as SJ2285.

Integration

SJ2285 was streaked on LB plates with 10 µg/ml kanamycin and incubated at 50° C. overnight.

10 colonies formed at 50° C. were propagated in TY medium at 30° C. to allow excision and loss of the integrated plasmid. Following one transfer in TY medium, Kana$^R$ erm$^S$ colonies were found by replica plating of the cultures derived from 7 of the 10 integrant colonies.

Amplification (as in example 1) was attempted with 4 of these strains, and isolates eventually growing in 2000 µg/ml kanamycin obtained from 3 of these 4.

One amplified series was kept:

| Kanamycin concentration µg/ml | Strain |
|---|---|
| 10 | SJ2322 |
| 20 | SJ2323 |
| 50 | SJ2324 |
| 100 | SJ2325 |
| 200 | SJ2326 |
| 500 | SJ2327 |
| 1000 | SJ2328 |
| 1500 | SJ2329 |
| 2000 | SJ2330 |

SJ2323-SJ2326 were inoculated from SJ2322 (100 µl in 10 ml), and SJ2327-SJ2330 were inoculated from SJ2326. Aliquots of all cultures were frozen in 15% glycerol, and cells harvested for preparation of chromosomal DNA.

Southern analysis of chromosomal DNA from strains SJ2324 and SJ2328 digested by EcoRI revealed a 5.5 kb fragment as expected from the amplification of the amyL-cgtA+kanamycin resistance genes. The 5.5 kb fragment from strain SJ2328 was very conspicuous already in the EtBr-stained agarose gel.

Yield Effect of Amplification

Shake flasks with BPX medium were inoculated directly from the glycerol-frozen cultures, and shaken at 300 rpm at 37° C. The CGTase yields obtained with the amplified strains were compared to the yield obtained with strain SJ1707.

| Strain | Kanamycin µg/ml | exp. A 7 days Rel. Yield | exp. B 7 days Rel. Yield | exp. C 8 days Rel. Yield |
|---|---|---|---|---|
| SJ1707 | 0 | | 1.0 | 1.1 |
| SJ2322 | 0 | 2.1 | 1.4 | |
| | 10 | 2.2 | 1.7 | |
| SJ2323 | 0 | 1.9 | | |
| | 20 | 2.0 | | |
| SJ2324 | 0 | 2.2 | 1.5 | 1.5 |
| | 50 | 2.4 | 1.7 | 1.8 |
| SJ2325 | 0 | 1.8 | | |
| | 100 | 1.6 | | |
| SJ2326 | 0 | 1.6 | | |
| | 200 | 1.8 | | |
| SJ2327 | 0 | 1.9 | | |

-continued

| Strain | Kana-mycin μg/ml | exp. A 7 days Rel. Yield | exp. B 7 days Rel. Yield | exp. C 8 days Rel. Yield |
|---|---|---|---|---|
| SJ2328 | 500 | 1.3 | | |
| | 0 | 1.9 | 1.6 | 1.4 |
| | 1000 | 2.4 | 2.0 | 2.1 |

It is apparent that the amplified strains produce more CGTase than does the parent strain.

The stability of some of the strains from shake flasks without kanamycin was checked by platings on LB plates containing starch and scoring for halo formation. The ultimate effect of genetic instability would be loss of even the last copy of the CGTase gene, resulting in CGTase negative segregants which would be unable to produce halos on starch plates.

SJ2322:
  100/100 positive (exp. A)
  300/300 positive (exp. B)
SJ2324:
  100/100 positive (exp. A)
  300/300 positive (exp. B)
  120/120 positive (exp. C)
SJ2328:
  200/200 positive (exp. A)
  500/500 positive (exp. B)
  120/120 positive (exp. C)

None of the strains investigated lost the last copy of the CGTase gene under the conditions tested.

REFERENCES

Jørgensen et al. (1990). In vivo genetic engineering: homologous recombination as a tool for plasmid construction. Gene 96, 37–41.

Horinouchi, S. and Weisblum, B. (1982b). Nucleotide sequence and functional map of pE194, a plasmid that specifies inducible resistance to macrolide, lincosamide, and streptogramin type B antibiotics. J. Bacteriol., 150, 804–814.

B. Diderichsen, (1986), Bacillus: Molecular Genetics and Biotechnology Applications, A. T. Ganesan and J. A. Hoch, Eds., Academic Press, pp. 35–46.

Sambrook et al. (1989) Molecular Cloning: a laboratory manual. 2nd edition

Beaucage et al., Tetrahedron Letters 22, 1981, pp. 1859–1869.

Matthes et al., EMBO Journal 3, 1984, pp. 801–805

Saiki et al. (1988), Science 239, 1988, pp. 487–491.

Diderichsen et al. (1990). Cloning of aldB, which encodes α-acetolactate decarboxylase, an exoenzyme from Bacillus brevis. J. Bacteriol., 172, 4315–4321.

Kieser, T. (1984), Factors affecting the isolation of CCC DNA from Streptomyces lividans and Escherichia coli. Plasmid 12, 19–36.

Akamatzu et al. (1984), An improved method of protoplast regeneration for Bacillus species and its application to protoplast fusion and transformation. Agric. Biol. Chem. 48, 651–655.

Yasbin et al. (1975), J. Bacteriol. 121, 296–304.

I claim:

1. A method of amplifying in vivo a DNA sequence B present in a genome of a parent prokaryotic cell, comprising
 a) integrating in a genome of said cell a DNA construct comprising the structure C-M-A-D, in which
  A denotes a DNA sequence which is homologous with a genomic DNA fragment either flanking or overlapping the DNA sequence B to be amplified or being a subsequence of the DNA sequence B constituting one of the ends of said sequence B,
  C denotes a DNA sequence which is homologous with a genomic DNA fragment either flanking or overlapping the DNA sequence B to be amplified or being a subsequence of the DNA sequence B constituting one of the ends of said sequence B, the sequence C being located in the opposite end of the sequence B as compared to A,
  D denotes a DNA sequence which is homologous with a genomic DNA fragment located distal for C as compared to B, and
  M denotes a DNA sequence encoding a selection marker,
 b) selecting for cells in which the DNA sequence M has been integrated in the genome either upstream or downstream of the DNA sequence B together with the sequence A, which cells comprise, in any orientation, the structure A-B-C-M-A-D, and
 c) propagating the cells selected in step b) under increasing selection pressure for the selection marker encoded by the DNA sequence M so as to obtain a cell which has obtained an increased number of genomically integrated copies of the DNA sequences B and M as compared to the parent cell.

2. The method according to claim 1, in which the DNA construct is carried on a suitable vector.

3. The method according to claim 2, in which the vector is a plasmid or a phage.

4. The method according to claim 2, in which the vector is temperature-sensitive for replication.

5. The method according to claim 4, in which the vector further carries a DNA sequence encoding a selection marker.

6. The method according to claim 1, in which the parent cell is a microbial cell, a plant cell, an insect cell, a vertebrate cell, or a mammalian cell.

7. The method according to claim 6, in which the parent cell is a bacterial or a fungal cell.

8. The method according to claim 7, in which the bacterial cell is a cell of a gram-positive bacterium or a cell of a gram-negative bacterium and the fungal cell is a yeast cell or a cell of a filamentous fungus.

9. The method according to claim 1, in which the DNA sequence B comprises an open reading frame.

10. The method according to claim 9, in which the DNA sequence B further comprises one or more regulatory signals.

11. The method according to claim 9, in which the DNA sequence B is a single gene, a cluster of genes or an operon.

12. The method according to claim 8, in which the DNA sequence B is heterologous to the parent cell and derived from a microorganism, a plant, an insect, a vertebrate or a mammal.

13. The method according to claim 12, in which the DNA sequence B is derived from a bacterium or a fungus.

14. The method according to claim 8, in which the DNA sequence B encodes an enzyme, a hormone, an antigenic component, an immunoactive protein or peptide, a growth factor, an allergen, a tumor associated antigen, or a blood protein.

15. The method according to claim 8, in which the DNA sequence B comprises one or more genes encoding a biosynthetic pathway, one or more genes encoding elements of the cell transcription, translation or protein secretion apparatus a regulatory factor acting in the cell or a metal resistance, or B complements an auxotrophic mutation of the host cell.

16. The method according to claim 1, in which the DNA sequence B is a gene and the DNA sequence A is homologous to a full or partial promoter sequence upstream of the coding part of the DNA sequence B.

17. The method according to claim 1, in which the DNA sequence M encodes a product which confers antibiotic resistance to the parent cell, which confers prototrophy to an auxotrophic cell, or which complements a defect of the parent cell.

18. The method according to claim 17, in which the antibiotic resistance is a resistance to kanamycin, tetracyclin, ampicillin, erythromycin, or chloramphenicol.

19. The method according to claim 17, in which the DNA sequence M encodes a product which confers resistance to a heavy metal.

* * * * *